United States Patent
Chen et al.

(10) Patent No.: US 8,927,462 B2
(45) Date of Patent: Jan. 6, 2015

(54) METHOD FOR IDENTIFYING HLA COMPLEXES ASSOCIATED WITH ADVERSE DRUG REACTIONS

(75) Inventors: Yuan-Tsong Chen, Taipei (TW); Shuen-Iu Hung, Changhwa (TW); Chun-Yu Wei, Taipei (TW)

(73) Assignees: Academia Sinica, Taipei (TW); National Yang-Ming University, Taipei (TW)

(*) Notice: Subject to any disclaimer, the term of this patent is extended or adjusted under 35 U.S.C. 154(b) by 482 days.

(21) Appl. No.: 13/083,866

(22) Filed: Apr. 11, 2011

(65) Prior Publication Data

US 2011/0251074 A1 Oct. 13, 2011

Related U.S. Application Data

(60) Provisional application No. 61/323,067, filed on Apr. 12, 2010.

(51) Int. Cl.
C40B 30/04 (2006.01)
G01N 33/569 (2006.01)

(52) U.S. Cl.
CPC .............................. *G01N 33/56977* (2013.01)
USPC ........................................................... 506/9

(58) Field of Classification Search
None
See application file for complete search history.

(56) References Cited

U.S. PATENT DOCUMENTS

| 5,550,039 | A | 8/1996 | Trachtenberg |
| 5,883,238 | A | 3/1999 | Andrien |
| 6,583,139 | B1 | 6/2003 | Thorsett et al. |
| 7,470,513 | B2 | 12/2008 | Chen et al. |
| 7,902,121 | B2 | 3/2011 | Chen et al. |
| 2004/0137537 | A1 | 7/2004 | Montero-Julian et al. |
| 2005/0100926 | A1 | 5/2005 | Chen et al. |
| 2006/0228759 | A1 | 10/2006 | Muchhal et al. |
| 2009/0053727 | A1 | 2/2009 | Chen et al. |

FOREIGN PATENT DOCUMENTS

| CN | 1995383 | 7/2007 |
| WO | WO-2007/032761 | 3/2007 |
| WO | WO2007/134235 | 11/2007 |

OTHER PUBLICATIONS

Wu et al. (Jul. 2006) Journal of Allergy and Clinical Immunology vol. 118 pp. 233 to 241.*
Soen et al. (Dec. 22, 2003) PLoS Biology vol. 1 pp. 429 to 438.*
Kuroki et al. (Jul. 13, 2005) Human Molecular Genetics vol. 14 pp. 2469 to 2480.*
Yang, C. et al. "HLA-B*1502-bound peptides: implications for the pathogens is of carbamazepine-induced Stevens-Johnson syndrome"; J. Allergy Clin. Immunol.; 120(4):870-877 (2007).
Chen, P. et al. "Carbamazepine-induced toxic effects and HLA-B*1502 screening in Taiwan"; N. Engl. J. Med.; 364(12)1126-1133 (2011).
Alfirevic A, et al "HLA-B locus in Caucasian patients with caramazepine hypersensitivity." *Pharmacogenomics*. Sep. 2006; 7(6):813-8.

(Continued)

*Primary Examiner* — Christian Boesen
(74) *Attorney, Agent, or Firm* — Cesari and McKenna, LLP (57) ABSTRACT

A method for identifying from an HLA library an HLA complex that specifically binds to a compound. This method can be relied on to assess whether a compound is likely to induce an adverse drug reaction and, if so, in which human population.

19 Claims, 6 Drawing Sheets

(56) References Cited

OTHER PUBLICATIONS

Bigby et al. (1986) Drug-induced cutaneous reactions. A report from the Boston Collaborative Drug Surveillance Program on 15,438 consecutive inpatients, 1975 to 1982. *JAMA.* 256(24):3358-3363.
Chan et al. "HLA and allopurinol drug eruption" *Dermatologica.* 1989, 179(1):32-3.
Chung et al (2004). Medical genetics: a marker for Stevens-Johnson syndrome. *Nature.* 428(6982):486.
Deng et al. LOD score exclusion analyses for candidate genes using random population samples. *Ann Hum Genet*, May 2001;65(Pt 3):313-29.
Edwards et al. Concordance of primary generalized epilepsy and carbamazepine hypersensitivity in monozygotic twins. *Postgrad Med J.* 1999, 75(889):680-1.
Feltkamp et al. Spondyloarthropathies in eastern Asia. *Curr Opin Rheumatol.* 2001, 13(4):285-90.
Gennis et al. Familial occurrence of hypersensitivity to phenytoin. *Am J Med.* 1991, 91(6):631-4.
Green et al. Genetic analysis of microsomal epoxide hydrolase in patients with carbamazepine hypersensitivity. *Biochem Pharmacol.* 1995, 50(9):1353-9.
Gumperz et al. (1995). The Bw4 public epitope of HLA-B molecules confers reactivity with natural killer cell clones that express NKB1, a putative HLA receptor. *J Exp Med.* 181(3):1133-1144.
Gut, J. (2002). Severe adverse drug reactions and theragenomics. *Business Briefing Pharmatech.* Retrieved from the Internet: URL: http://jlglex.com/TheragenomicArticle3.pdf> Retrieved on Dec. 19, 2007.
Hari et al. T cell involvement in cutaneous drug eruptions. *Clin Exp Allergy.* 2001, 31(9):1398-1408.
Hildesheim et al. (2002). Association of HLA class I and II alleles and extended haplotypes with nasopharyngeal carcinoma in Taiwan. *J Natl Cancer Inst.* 94(23):1780-1789.
Hiratsuka M., et al, Competitive allele-specific short oligonucleotide hybridization (CASSOH) with enzyme-linked immunosorbent assay (ELISA) for the detection of pharmacogenetic single nucleotide polymorphisms (SNPs). J of Biochemical and Biophysical Methods, 67:87-94 (2006).
Hung et al. HLA-B genotyping to detect carbamazepine-induced Stevens-Johnson syndrome: implications for personalizing medicine. *Personalized Medicine.* Aug. 2005, vol. 2, No. 3, pp. 225-237.
Juppner, H. Functional properties of the PTH/PTHrP receptor. *Bone.* Aug. 1995; 17(2 Suppl):39S-42S.
Khan, MA. Update: the twenty subtypes of HLA-B27. *Curr Opin Rheumatol.* 2000, 12(4):235-8.
Lazarou et al. (1998) Incidence of adverse drug reactions in hospitalized patients: a meta-analysis of prospective studies. *JAMA.* 279(15):1200-1205.
Leeder, JS. Mechanisms of idiosyncratic hypersensitivity reactions to antiepileptic drugs. *Epilepsia.* 1998, 29 Suppl 7:S8-16.
Lonjou et al. A marker for Stevens-Johnson syndrome . . . : ethical matters. *Pharmacogenomics Journal.* (2006) 6, 265-268; published online Jan. 17, 2006.
Mallal et al. (2002). Association between the presence of HLA-B*5701, HLA-DR7, and HLA-DQ3 and hypersensitivity to HIV-I reverse transcriptase inhibitor abacavir. *Lancet.* 359(9308):727-732.
Naisbitt et al. Hypersensitivity reactions to carbamazepine: characterization of the specificity, phenotype, and cytokine profile of drug-specific T cell clones. *Mol Pharmacol.* 2003, 63(3):732-41.
Nassif et al. (2002). Drug specific cytotoxic T-cells in the skin lesions of a patient with toxic epidermal necrolysis. *J Invest Dermatol.* 118(4):728-733.
Pichler et al. High IL-5 production by human drug-specific T cell clones. *Int Arch Allergy Immunol.* 1997, 113(1-3):177-80.
Pirmohamed et al. TNFα promoter region gene polymorphisms in carbamazepine-hypersensitive patients. *Neurology.* 2001, 56(7): 890-6.
Pirmohamed et al (2003). Adverse drug reactions: back to the future. *Br J Clin Pharmacol.* 55(5):486-492.
Romphruk et al (2003). HLA-B*15 subtypes in the population of north-eastern Thailand. *Eur J Immunogenet.* 30(2):153-158.
Roujeau et al. HLA phenotypes and bullous cutaneous reactions to drugs. *Tissue Antigens.* 1986, 28(4):251-4.
Roujeau et al. Genetic susceptibility to toxic epidermal necrolysis. *Arch Dermatol.* 1987, 123(9):1171-3.
Roujeau, JC. The spectrum of Stevens-Johnson syndrome and toxic epidermal necrolysis: a clinical classification. *J Invest Dermatol.* 1994, 102(6):28S-30S.
Roujeau et al. Severe adverse cutaneous reactions to drugs. *N Engl J Med.* 1994, 331(19):1272-85.
Roujeau et al. Medication use and the risk of Stevens-Johnson syndrome or toxic epidermal necrolysis. *N Engl J Med.* 1995, 333(24):1600-7.
Sankar, P., Medline definitions of race and ethnicity and their application to genetic research. *Nature Genetics* (2003), vol. 34, p. 119.
Shirato et al. Stevens-Johnson syndrome induced by methazolamide treatment. *Arch Ophthalmol.* 1997, 115(4):550-3.
Svensson et al. Cutaneous drug reactions. *Pharmacol Rev.* 2000, 53(3):357-379.
Thisted, RA. What is a P-value? (1998). Available online at http://www.stat.uchicago.edu/~thisted/Distribute/pvalue.pdf> Retrieved on Dec. 19, 2007.
Wolkenstein et al. A slow acetylator genotype is a risk factor for sulphonamide-induced toxic epidermal necrolysis and Stevens-Johnson syndrome. *Pharmacogenetics.* 1995, 5(4):255-8.
Yates et al. Molecular diagnosis of thiopurine S-methyltransferase deficiency: genetic basis for azathioprine and mercaptopurine intolerance. *Annals of Internal Med.* 1997, 126(8):608-14.
Hung et al., Pharmacogenetics and Genomics, vol. 16(4), pp. 297-306 (2006).
Hung et al., Proceedings of the National Academy of Sciences of the United States of America, vol. 102(11), pp. 4139-7139 (2005).
Misra, et al. (Postgrad Med J 2003 vol. 39 p. 703).
Chung, et al. (Nature Apr. 2004 vol. 428 p. 486).
Futami, et al. (Digestive Diseases and Sciences 1995 vol. 40 p. 814).
Leeder (Epilepsia 1998 vol. 39 Suppl 7:S8-16).
Lim, et al. (Neurology Asia 2008 vol. 13 p. 15).
Hoa BK et al. Tissue Antigens, 71:127-134 (2007).
Hegele, R.A. Arterioscler Thromb Vasc Biol. 2002(22):1058-1061.
Pennisis E. et al. Science (1998) vol. 281(5384):1787-1789.
Carbamazepine-oral Tegretol (cont.), from www.medicientnet.com, printed on Jul. 9, 2012, 1 page.
Wu. et al., "Activation of T cells by carbamazepine and carbamazepine metabolites", Journal of Allergy and Clinical Immunology, vol. 118, 2006.
Lun, et al., "Harvesting Candidate Genes Responsible for Serious Adverse Drug Reactions from a Chemical-Protein Interactome", PLOS Computational Biology, vol. 5, No. 7, Jul. 2009.

* cited by examiner

METHOD FOR IDENTIFYING HLA COMPLEXES ASSOCIATED WITH ADVERSE DRUG REACTIONS

CROSS-REFERENCE TO RELATED APPLICATION

This application claims priority to U.S. Provisional Application No. 61/323,067, filed on Apr. 12, 2010. The content of the prior application is incorporated herein by reference in its entirety.

BACKGROUND OF THE INVENTION

Adverse drug reactions (ADRs) remain a major problem in both medical practice and pharmaceutical industry. Among the many types of ADRs, Stevens-Johnson syndrome (SJS), toxic epidermal necrolysis (TEN), and hypersensitivity syndrome (HSS) are the most serious and life-threatening conditions with SJS and TEN still carry 10-50% mortality rate. See, Roujeau et al., New Engl. J. Med. 333:1600-1607 (1995). Although the incidence of SJS/TEN/HSS is low, these conditions can kill or severely disable previously otherwise healthy people. For the pharmaceutical industry, occurrence of severe drug hypersensitivity can be detrimental; a few cases have prompted the withdrawal of newly released drugs from the market. See the world wide web at fda.gov/safety/recalls/default.htm.

Certain class I HLA alleles (e.g., HLA-A and HLA-B alleles) and certain class II HLA alleles (e.g., HLA-DR alleles) have been found to be associated with ADRs. See, Chung et al., Nature. 428:486 (2004); Hung et al., Proc. Natl. Acad. Sci. U.S.A. 102:4134-4139 (2005); Chessman et al., Immunity. 28, 822-832 (2008); Daly et al., Nat. Genet. 41:816-819 (2009); Singer et al., Nat. Genet. 42:711-714 (2010); Mallal et al., New Engl. J. Med. 358:568-579 (208); Romano et al., Ann. Allergy Asthma. Immunol. 80: 433-437 (1998); Kim et al., Clin. Exp. Allergy 35:339-344 (2005); Flung et al., Pharmacogenet. Genomics 16: 297-306 (2006); Dettling et al., Pharmacogenomics J. 7: 325-332 (2007); O'Donohue et al., Gut 47:717-720 (2000); Lonjou et al., Pharmacogenet. Genomics 18: 99-107 (2008); Kim et al., Pharmacogenomics 11: 879-884(2010); Martin et al., AIDS 19: 97-99 (2005); Littera et al., AIDS 20: 1624-1626 (2006): Locharernkul et al., Epilepsia 49:2087-2091 (2008); and Kindmark et al., Pharmacogenomics J. 8: 186-195 (2008). All of these ADR-HLA allele associations were determined in patients suffering from an ADR induced by an approved drug. At present, there is no method that can be used to predict whether a candidate drug under development will develop these life-threatening conditions, such as SJS/TEN/HSS in human.

As development of a new drug can cost on average 1 billion dollars and 10 years of time, it would be of tremendous value to develop a screening method useful in predicting the safety profile of a candidate drugs at an early stage of drug development.

SUMMARY OF THE INVENTION

The present invention relates to a method for identifying from an HLA library an HLA complex, if any, that binds to a compound. This method can be relied on to predict whether a compound would induce an adverse drug reaction and, if so, in which human population.

The method of this invention includes at least four steps: (i) providing an HLA library (e.g., a class I or class II HLA library) including a plurality of HLA complexes (e.g., soluble HLA complexes) located at a plurality of addresses on a support member, each of the HLA complexes being assigned to a distinct address, (ii) contacting a compound with the HLA complexes, (iii) determining whether the compound binds to an HLA complex in the library, and, if so, (iv) identifying the HLA complex that binds to the compound based on the address of that HLA complex. The term "a district address" used herein refers to a spot on a support member, at which one and only one type of HLA complex is located.

In one example, the HLA library is a microchip-based library including various HLA complexes attached to a support member. In this case, the determining step can be performed by Surface Plasmon Resonance (SPR). In another example, the HLA library is a cell-based library including a plurality of cell lines each expressing a particular HLA complex. Each cell line can be prepared by expressing an HLA complex in a parent cell, which preferably is deficient in at least one type of HLA (e.g., class I HLA). In this case, the determining step can be performed by collecting the HLA complex from each address and determining whether the HLA complex binds to the compound by mass spectrometry. Alternatively, the compound can be labeled by an isotope and the determining step is performed by examining radioactivity at each address.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

DETAILED DESCRIPTION OF THE INVENTION

Described herein is a method of screening for an HLA complex, if any, that specifically interacts with a compound (e.g., a small molecule drug or drug candidate), using an HLA library. This method can be used to assess the probability of the compound for inducing an adverse drug reaction and also to identify the human population (i.e., those carrying the HLA complex identified in this method) with an increased risk for developing drug hypersensitivity in response to the test compound. As such, it is of particular importance in new drug development as it helps predict whether a drug candidate is likely to cause adverse drug reaction and, if so, in which patient population.

The HLA library used in the method of this invention can be a class I library including one or more subgroups of HLA complexes (e.g., an HLA B library). HLA-B alleles are one of the most polymorphic genes with more than 800 variants. See Marsh and Who Nomenclature Committee for Factors of the Hla System, Hum. Immunol. 71(4):432-6; 2010. If necessary, an HLA-B library can include all of the known 800+ different HLA-B complexes. The HLA library can also be a class II library including one or more subgroups of class II HLA complexes (e.g., an HLA-DR library). Alternatively, it can contain both class I and class II HLA complexes. When necessary, any of the above-described libraries can be expanded to include new HLA complexes.

Both class I and class II HLA alleles are well known in the art. For example, these alleles can be retrieved from GenBank or the database provided by the HUGO Gene Nomenclature Committee, EMBL Outstation—Hinxton, European Bioinformatics Institute, Wellcome Trust Genome Campus Hinxton Cambridge CB10 1SD, UK (see the world wide web at genenames.org).

The method of this invention can be performed using either a cell-based or a microchip-based HLA library.

Cell-Based HLA Library

A cell-based HLA library contains a plurality of cell lines each producing a distinct HLA complex. Each cell line can be prepared by genetically modifying a parent cell (preferably a mammalian cell) for expressing (a) a class I HLA α chain and optionally, β2-microglobulin (if the patent cell does not express endogenous β2-microglobulin), or (b) a class II HLA α chain and a class II HLA β chain, via conventional recombinant technology. Preferably, the parent cell for constructing the library is deficient in at least one type of HLA alleles, e.g., class I HLA, class II HLA, or a subgroup thereof. Such cell lines include, but are not limited to, ATCC CRL-1993 (C1R), ATCC CRL-2309 (KerTr), ATCC CRL-1992 (T2), ATCC CRL-2134 (LS513), ATCC CRL-2158 (LS1034), ATCC CRL-2159 (LS411N), ATCC CRL-2547 (Panc 10.05), ATCC CRL-2551 (Panc 08.13), ATCC CRL-2553 (Panc 02.03), ATCC CRL-2549 (Panc 03.27), ATCC CRL-2554 (Panc 02.13), ATCC CRL-2555 (Panc 04.03), and ATCC CRL-2557 (Panc 05.04). In this list, the first two cell lines are class I HLA deficient and the remaining cell lines are class II HLA deficient.

Transfected cells stably expressing the desired HLA molecules can be selected via routine procedures. A stable cell line that produces a high level of a class I HLA complex (composed of a class I HLA α chain and β2-microglobulin) or a class II complex (composed of a class II HLA α chain and a class II HLA β chain) can be selected as a member of the cell-based HLA library. In one example, the selected cell line expresses full-length HLA molecules. In another example, it expresses fragments of HLA molecules that include their extracellular domains. Such a cell line produces a soluble HLA complex.

Following the procedures described above, cell lines expressing various HLA complexes, each cell line producing one type of HLA complex, can be constructed. The various HLA complexes can include class I HLA (e.g., HLA-A, HLA-B, HLA-C, HLA-E, HLA-F, HLA-G, HLA-K, HLA-L, or a combination thereof), class II HLA (e.g., HLA-DP, HLA-DQ, HLA-DR, HLA-DM, HLA-DO, or a combination thereof). These stable cell lines form a cell-based HLA library.

Figure 1:
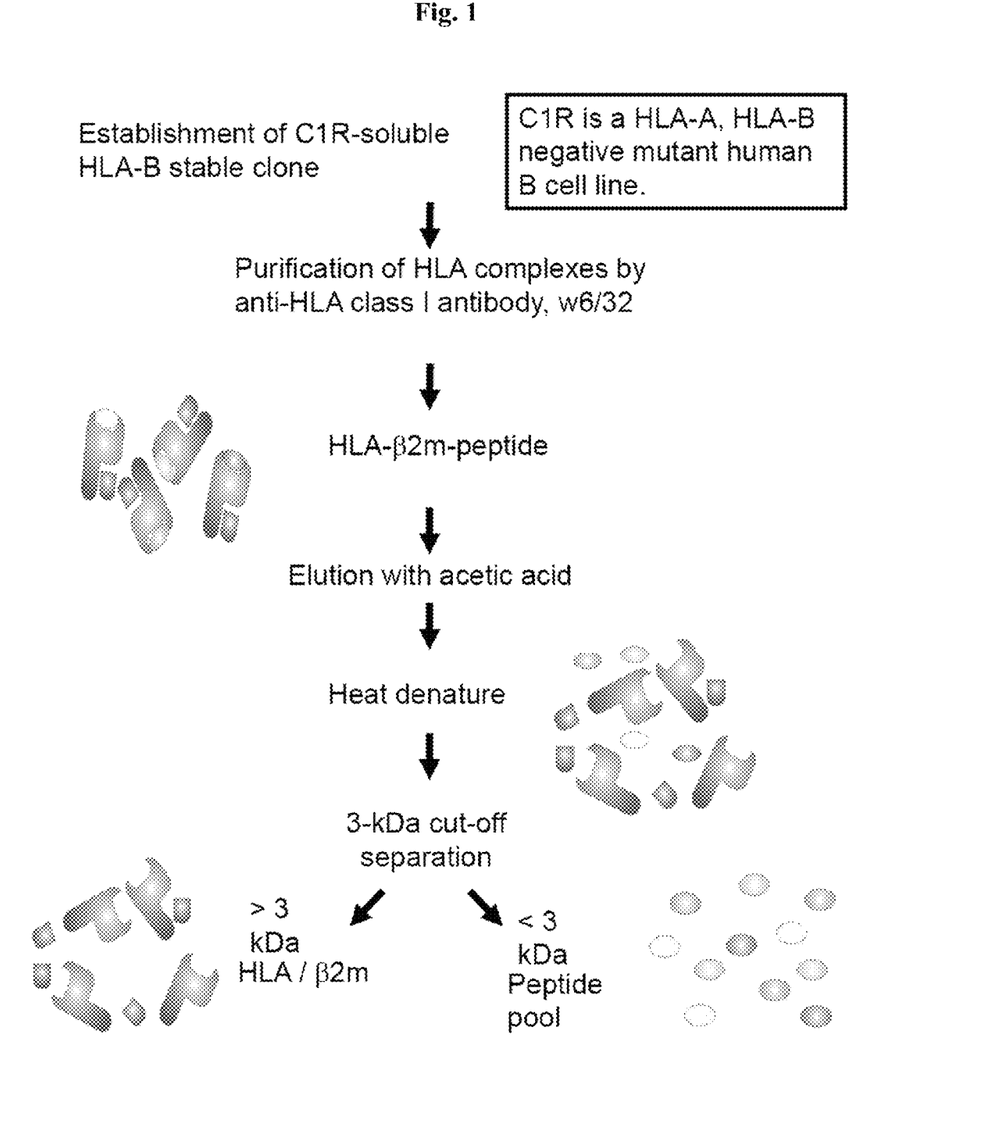
FIG. 1 is a scheme illustrating a process of obtaining peptides capable of binding to an HLA-B-β2 microglobulin complex produced in C1R cells that stably express a soluble HLA-B molecule.

Each of the stable cell lines can be placed in a well (i.e., a distinct address) of a support member. To perform the screening method described herein, each of the cell lines is incubated with a test compound for a suitable period. The cells are then washed to remove free molecules of the compound and then examined to determine whether the HLA complexes expressed by them bind to the compound. See FIG. 1 In one example, the compound is labeled by a radioactive isotope and binding between the compound and an HLA complex is determined based on the radioactivity level in each well relative to a blank control. If the radioactivity level in a well is greater than the blank control, it indicates that the HLA complex produced by the cells in that well is capable of binding to the compound.

When cell lines producing soluble HLA complexes are used, their binding to a test compound can be determined as follows. After cells are treated with a test compound, the supernatant in each well is collected and the soluble HLA complex is purified using an affinity column containing an HLA-specific agent (e.g., an antibody capable of binding to all types of class I or class II HLA). Samples containing purified HLA complexes are heated at a suitable temperature (e.g., 70° C.) for 10 minutes to dissociate the binding between the compound (which may attached to a peptide) and the HLA complex. Fractions containing low-molecule weight components (e.g., <3-kDa) are collected, e.g., using a centrifugal filter, 3-kDa cutoff (Amicon Ultra-4, Millipore) and subjected to liquid chromatography-tandem mass spectrometry to determine whether they contain the test compound.

It is known that presentation of certain drugs (e.g., abacavir and penicillin) by antigen-presenting cells (APC) are processing-dependent. Namely, after entering cells, these compounds covalently bind to carrier proteins, which are then processed and presented by APC cells. See, e.g., Chessman et al., Immunity. 28, 822-832 (2008); and Padovan et al., Eur. J. Immunol. 27; 1303-1307. (1997). The cell-based class I HLA library is particularly useful in screen for HLA complexes specific to compounds that are presented by APCs via a processing-dependent pathway.

Chip-Based HLA Library

A chip-based HLA library can be prepared by immobilizing various HLA complexes, preferably containing the extracellular domains of the HLA molecules, each on a distinct spot of a microchip, via a routine method. See, e.g., Nature Reviews Drug Discovery. 1:515-528 (2002). The various HLA complexes can be obtained from the stable cell lines described above.

To screen for an HLA complex capable of binding to a test compound, the various HLA complexes, attached to the microchip, can be incubated with the compound for a suitable period under conditions allowing binding of the compound to its cognate HLA complex. The chip is then washed to remove unbound compound molecules and then subjected to SPR measurement to identify a compound-bound HLA complex. After an HLA complex is found to bind to a test compound, its identity can be determined based on its address on the chip.

Figure 2:
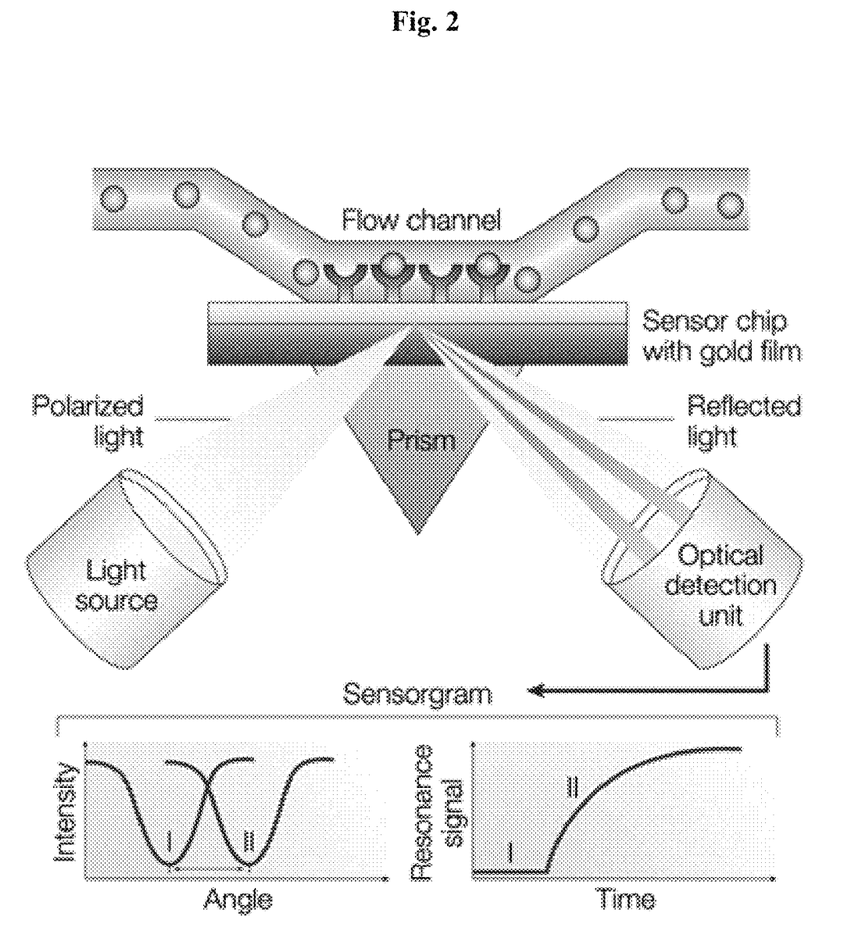
FIG. 2 is a scheme illustrating the Surface Plasmon Resonance assay.

SPR is a high throughput, label-free interaction analysis system, and are used in areas such as pharmaceutical drug discovery, antibody characterization, proteomics, immunogenicity, biotherapeutic development and manufacture, and many life science research applications. Surface plasmon resonance (SPR) detects changes in the refractive index in the immediate vicinity of the surface layer of a sensor chip. SPR is observed as a sharp shadow in the reflected light from the surface at an angle that is dependent on the mass of material at the surface. The SPR angle shifts (from I to II in the lower left-hand diagram) when biomolecules bind to the surface and change the mass of the surface layer. This change in resonant angle can be monitored non-invasively in real time as a plot of resonance signal (proportional to mass change) versus time. See FIG. 2.

Use of the chip-based HLA library can identify HLA complexes specific to compounds that are presented by APCs via a processing-independent pathway, i.e., binding directly to HLA complexes. See, e.g., Wu et al., J. Allergy Clin. Immunol. 118:233-241 (2006); Schnyder et al., J. Clin. Invest. 100:136-141 (1997); and Naisbitt et al., J. Allergy Clin. Immunol. 111:1393-1403 (2003).

If no HLA complex that binds to a test compound is identified in the method of this invention, it indicates that this compound has a low probability to induce an ADR. On the other hand, if an HLA complex that binds to a test compound is identified in this method, it indicates that the test compound has a high probability of inducing an ADR, particularly in humans expressing that HLA complex.

It is known in the art that certain HLA alleles have higher frequencies in particular human ethnic groups than others. See world wide web at allelefrequencies.net. Based on this knowledge, the result obtained from the method of this invention can be used to predict which ethnic group(s) would be sensitive to a particular drug or drug candidate. This will guide drug development with respect to patient selection in clinical trials and marketing decision.

Table 1 below lists the major HLA-B alleles in Caucasians, Asians, and African Americans.

TABLE 1

Major HLA-B alleles in Caucasian, Asian and African American

| Caucasian[@] | Northern Asian | Southern Asian* | African American |
|---|---|---|---|
| B*0702 | B*0702 | B*0702 | B*0702 |
| B*0801 | B*1301 | B*0705 | B*0801 |
| B*1302 | B*1302 | B*1301 | B*1402 |
| B*1402 | B*1501 | B*1302 | B*1503 |
| B*1404 | B*1518 | B*1307 | B*1510 |
| B*1501 | B*2704 | B*1501 | B*1801 |
| B*1509 | B*3501 | B*1502 | B*3501 |
| B*1801 | B*3701 | B*1525 | B*4201 |
| B*2702 | B*3802 | B*1532 | B*4403 |
| B*2703 | B*3901 | B*1801 | B*4501 |
| B*2705 | B*4001 | B*1803 | B*5301 |
| B*3501 | B*4002 | B*2704 | B*5703 |
| B*3502 | B*4006 | B*2706 | B*5801 |
| B*3503 | B*4402 | B*3501 | B*5802 |
| B*3512 | B*4403 | B*3505 | |
| B*3517 | B*4601 | B*3701 | |
| B*3701 | B*4801 | B*3802 | |
| B*3801 | B*5101 | B*3901 | |
| B*3901 | B*5201 | B*3909 | |
| B*3905 | B*5401 | B*4001 | |
| B*3906 | B*5502 | B*4002 | |
| B*4001 | B*5603 | B*4003 | |
| B*4002 | B*5701 | B*4006 | |
| B*4006 | B*5801 | B*4014 | |
| B*4402 | | B*4403 | |
| B*4403 | | B*4601 | |
| B*4405 | | B*4801 | |
| B*4501 | | B*5101 | |
| B*4901 | | B*5401 | |
| B*5001 | | B*5501 | |
| B*5101 | | B*5502 | |
| B*5201 | | B*5601 | |

TABLE 1-continued

Major HLA-B alleles in Caucasian, Asian and African American

| Caucasian[@] | Northern Asian | Southern Asian* | African American |
|---|---|---|---|
| B*5301 | | B*5701 | |
| B*5501 | | B*5801 | |
| B*5701 | | | |
| B*5801 | | | |

[@]includes Hispanics and Jews
*does not include Indians

Without further elaboration, it is believed that one skilled in the art can, based on the above description, utilize the present invention to its fullest extent. The following specific example illustrates how to determine the binding between a compound, e.g., carbamazepine (CBZ), and an HLA-B complex (e.g., HLA-B*1502). It is to be construed as merely illustrative, and not limitative of the remainder of the disclosure in any way whatsoever. All publications cited herein are incorporated by reference.

Materials and Methods (i) Donor Characteristics

Blood samples were obtained from 8 CBZ-SJS/TEN and 1 CBZ-tolerant patients. All SJS/TEN patients were assessed via reviewing photographs, pathological slides and medical records by two dermatologists. A tolerant patient was one who received CBZ for at least 3 months without evidence of adverse reactions. Approvals were obtained from the hospitals' and Academia Sinica Institutional Review Board and informed consent was obtained from each participant.

(ii) Compounds

Three groups of compounds were used in this study. Group 1 includes CBZ, 10,11-epoxide CBZ (ECBZ, the major active metabolite of CBZ), oxcarbazepine (OXC), eslicarbazepine (ESL), 10-monohydroxy carbamazepine (MHD; major OXC and ESL active metabolite), and 5H-Dibenz[b,f]azepine (5HB), which has only the tri-cyclic ring structure. Group 2 includes other aromatic antiepileptic drugs (AEDs), such as, phenytoin (PHT), and Lamotrigine (LTG). Group 3 includes nonaromatice AEDs that share no common structure with CBZ, such as gabapentin (GAB), levetiracetam (LEV) and topiramate (TOP).

(iii) Cells

PBMC were isolated by the density-gradient Ficoll-Paque method according to the manufacturer's instructions (GE Healthcare Company, Piscataway, N.J., USA). CD8+ T cells from the CBZ-SJS patients were stimulated with 25 μg/ml CBZ for 11 to 14 days in vitro. After stimulation, the expanded T cells were then restimulated for 24 hr with the autologous B-Lymphblastoid cells (B-LCL) and CBZ. After 3~4 times of restimulation, CD8[+] T cells were sorted out for further functional assays. T cells were cultured with RPMI-HS medium consisted of RPMI 1640 supplemented with 10% heat-inactivated human type AB serum (Labquid Inc, Ontario, Calif.) and 50 U/ml IL-2 (R&D Systems, Minneapolis, Minn., USA). EBV-transformed B-cell lines (B-LCL) were generated by transforming the donor's PBMCs with supernatant from the EBV-producing cell lines B9-85.

(iv) Construction and Generation of Stable C1R Clones Expressing Soluble HLA-B*1502

To identify HLA-B*1502 drug-modified peptides, a C1R clone (C1R-HLA-B*1502) that stably expresses soluble HLA-B*1502 was established as described in Ou-Yang et al., J. Allergy Clin. Immunol. 120:870-877 (2007), by introducing a truncated HLA-B*1502 cDNA including exons 1-4 (coding for the extracellular domain of HLA-B*1502) into C1R cells. The HLA-B*1502 protein thus expressed was associated with the endogenous β2-microglobulin protein to form the HLA-B*1502 complex. C1R is a human B-lymphoblastoid cell line Hmy2.C1R (CRL-1993, American Type Culture Collection, Manassas, Va.) HLA class I deficient, no detectable HLA-A, a low level HLA-B35, normal expression of HLA-Cw4, and intact antigen processing and presentation pathways.

Briefly, the truncated HLA-B*1502 cDNA was obtained via PCR using a full-length HLA-B*1502 cDNA as a template and the following two primers:

```
forward primer 5PXI:
                                        (SEQ ID NO: 1)
5'-GGGCAAGCTTGGACTCAGAATCTCCCC-3' reverse primer 3PEI:
                                        (SEQ ID NO: 2)
5'-CCGCGAATTCTCATCTCAGGGTGAG-3'
```

These two primers include HindIII and EcoRI restriction sites. The truncated HLA-B*1502 cDNA, cloned into an expression plasmd, was introduced into C1R cells via electroporation, using the Biorad pulse system, at an initial pulse of 250V and 975 μF and a second pulse 30 seconds later under the same conditions. Transfected clones stably expressing soluble HLA-B*1502 were selected and expanded following conventional methods.

(v) Analyzing HLA-B-Bound Drug-Modified Peptides

CBZ (Novartis, Basel, Switzerland) dissolved in dimethylsulphoxide 50 mg/mL was added to a cell culture of the C1R-HLA-B*1502 clone described above at a final concentration of 50 μg/mL for 48 hours. The culture media were then collected, centrifuged, passed through a 0.45-μm membrane (Durapore; Millipore, Bedford, Mass.) to remove cell debris, and subjected to affinity chromatography with w6/32 monoclonal antibody-coupled CNBr-activated Sepharose 4B (Amersham, Piscataway, N.J.). The w6/32 monoclonal antibody is capable of binding to any class I HLA molecules. After recycling twice, the column was extensively washed with a PET buffer (20 mM phosphate buffer, 150 mM NaCl, 5 mM ethylenediaminetetraacetic acid, and 0.1% $NaN_3$ at pH 7.4) containing 10% saturated NaCl and 0.5% Nonidet P-40, PET buffer containing 5% of saturated NaCl and 0.5% Nonidet P-40, PET buffer, and phosphate-buffered saline. A complex containing the soluble HLA-B*1502 and β2-microglobulin were eluted with 0.2 N acetic acid, dialyzed, and stored at −80° C. Complexes containing soluble HLA-B*1501 or 1503 and β2-microglobulin were prepared following the same procedure described above. HLA-B*4001 and 5101 were purchased from PureProtein LLC (Okalahoma, Okla., USA).

A HLA-B-β-2-microglobulin complex were then heated at 70° C. for 10 minutes, and subjected to centrifugal filtration with a 3-kDa cutoff (Amicon Ultra-4; Millipore) to separate the HLA-B molecule and β2-microglobulin from any peptides binding to them. See FIG. 1. A fraction suspected of containing the peptides were then analyzed by liquid chromatography-tandem mass spectrometry.

(vi) [$^3$H] Incorporation Assay

Irradiated APCs ($10^3$) and T cells ($10^4$) were incubated with a test compound for 48 hours, and the proliferation of T cells was measured by incorporation of [$^3$H] thymidine. For fixation assay, autologous B-LCLs were pretreated with 0.05% paraformaldehyde for 30 s. For pulsing experiments, drugs were preincubated with B-LCLs overnight. B-LCLs were washed repeatedly to remove noncovalently bound drug, and then incubated with T cells.

(vii) $^{51}$Cr-Release Assays

B-LCLs, preincubated with IFN-γ (R&D Systems, Minneapolis, Minn., USA) overnight, were first incubated with $^{51}$Cr (Perkin Elmer, Waltham, Mass., USA) for 1 hr at 37° C. The treated cells were washed and resuspended in RPMI-FBS to a concentration of $1\times10^5$/mL, and 50 μl of the cells was added to each well in a 96-well V-bottomed plate, in the presence or absence of a test compound. 1% triton-X 100 (Sigma-Aldrich, St. Louis, Mo., USA) was used as a positive control. Cytotoxic T cells prepared via in vitro expansion of peripheral blood mononuclear cells (PBMCs) from patients, were included with the B-LCL cells for 4-hours. Radioactivity in the supernatant from each wells was measured by a Topcount (Packard Biosciences, Meriden, Conn., USA). The percentage of specific lysis was calculated as follows: ($^{51}$Cr release in the test well−spontaneous $^{51}$Cr release)/(maximum $^{51}$Cr release−spontaneous $^{51}$Cr release).

(viii) Surface Plasmon Resonance (SPR) Measurement and Analysis

Biacore T100 SPR biosensor was used for low-molecular-weight compound screening according to the manufacturer's protocol (GE Healthcare Company, Piscataway, N.J., USA). Briefly, 200 ng/ml purified HLA-B molecules in NaAc (pH 5.0) were coated on the CM5 chip using GE immobilization wizard with GE immobilization kits. PBS was used as running buffer and the flow rate was 10 μg/min. Drugs with different concentration dissolved in 5% DMSO in PBS were performed as analysts with 5% DMSO in PBS as running buffer. Responses from the compounds were corrected for DMSO effects. BIAevaluation Version 3.1 was used for data analysis.

Results (i) No Detection of Peptides Covalently Modified by Carbamazepine

The general patterns of peptides eluted from liquid chromatography were similar except for a peak that appeared at 83 minutes in the CBZ-treated sample but not in the CBZ-free sample. This peak was proved to be CBZ as it matches with the peak of pure CBZ generated in the same tandem mass spectrometry assay. The results obtained from this study indicate that CBZ does not covalently bind to peptides.

(ii) CBZ Recognition by HLA-B*1502 is Metabolic-Independent

Figure 3:
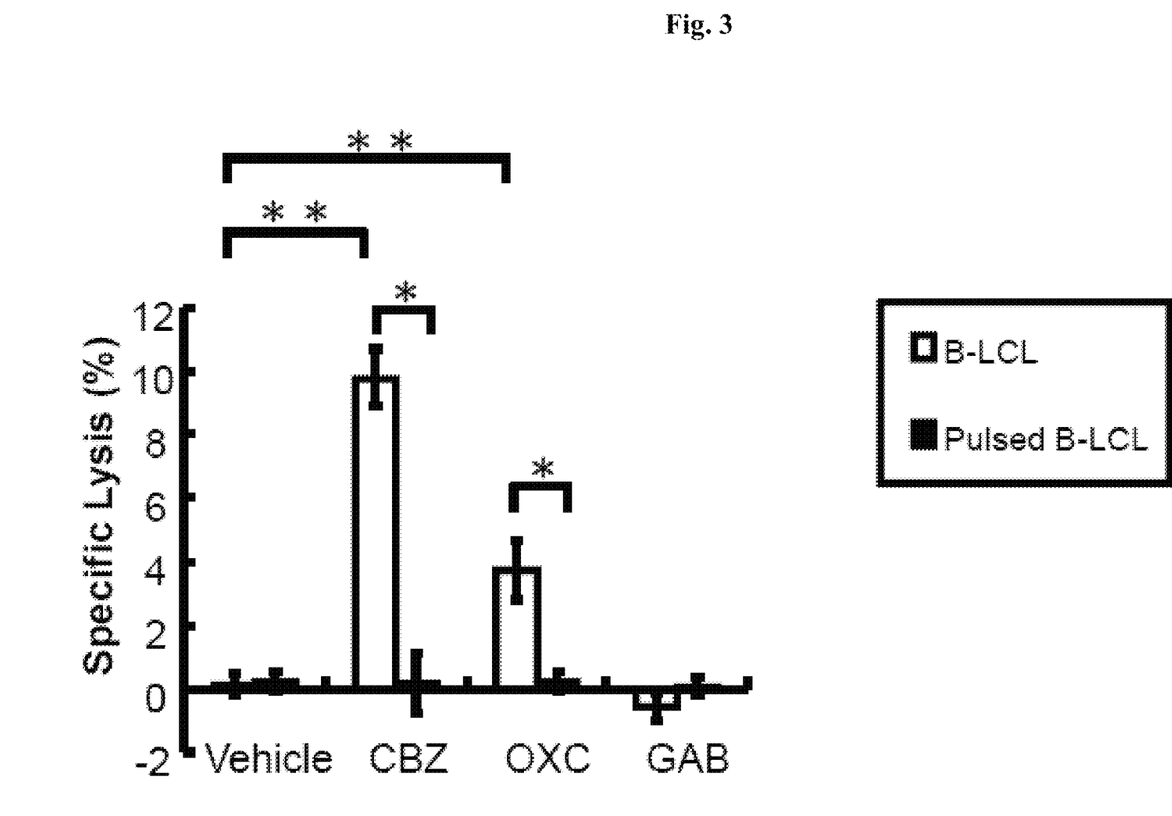
FIG. 3 is chart showing specific lysis of non-pulsed autologous B-LCL cells (open bar) or autologous B-LCL cells pulsed with 25 μg/ml CBZ, OXC, GAB, or a vehicle control (closed box) at 37° C. for overnight. Data from three patients were analyzed to obtain values of mean±SD. *: $p<0.05$ (non-pulsed B-LCL cells versus pulsed B-LCL cells). **: $p<0.001$ (drug-treated versus vehicle-treated groups).

As shown in FIG. 3, none of the CBZ-specific CD8$^+$ T cells responded to autologous B-LCL pulsed with CBZ overnight and washed out before the cytotoxicity assays. This result indicates that the recognition of CBZ by HLA-B1502 is metabolic-independent.

(iii) Presentation of CBZ by HLA-B*1502 is Processing-Independent

Figure 4:
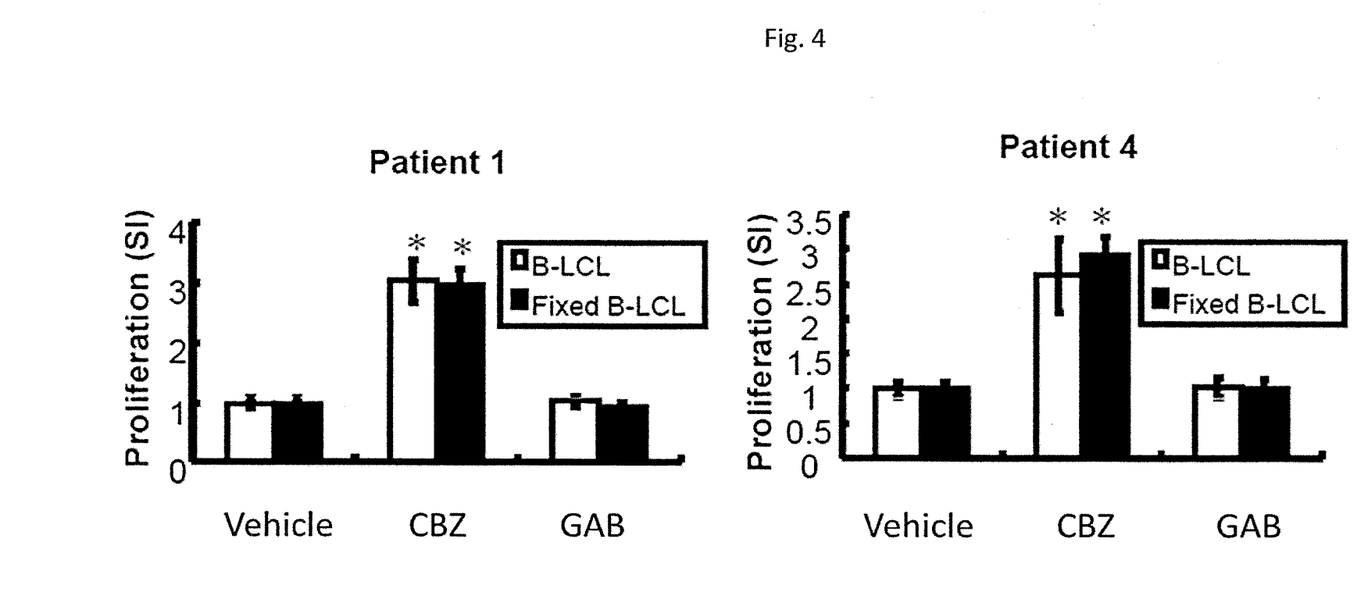
FIG. 4 is a chart showing autologous T cell proliferation in the presence of fixed (closed bar) and non-fixed (open bar) B-LCLs. T cell proliferation was determined by the conventional [$^3$H] thymidine incorporation assay. *: $p<0.05$ (drug-treated versus vehicle-treated groups)

To examine whether presentation of CBZ by the HLA-B*1502 would require cellular processing, autologous B-LCLs were fixed before incubation with CBZ and the activation of CBZ-specific CD8$^+$ T cells was monitored by their proliferation. CBZ was able to be presented by both fixed and unfixed autologous B-LCL and activated CBZ-specific CD8$^+$ T cells. See FIG. 4. In contrast, negative results were observed in cells treated with a vehicle control or GAB.

(iv) CBZ and Its Structure Analogs Directly Bind to HLA-B*1502

Figure 5:
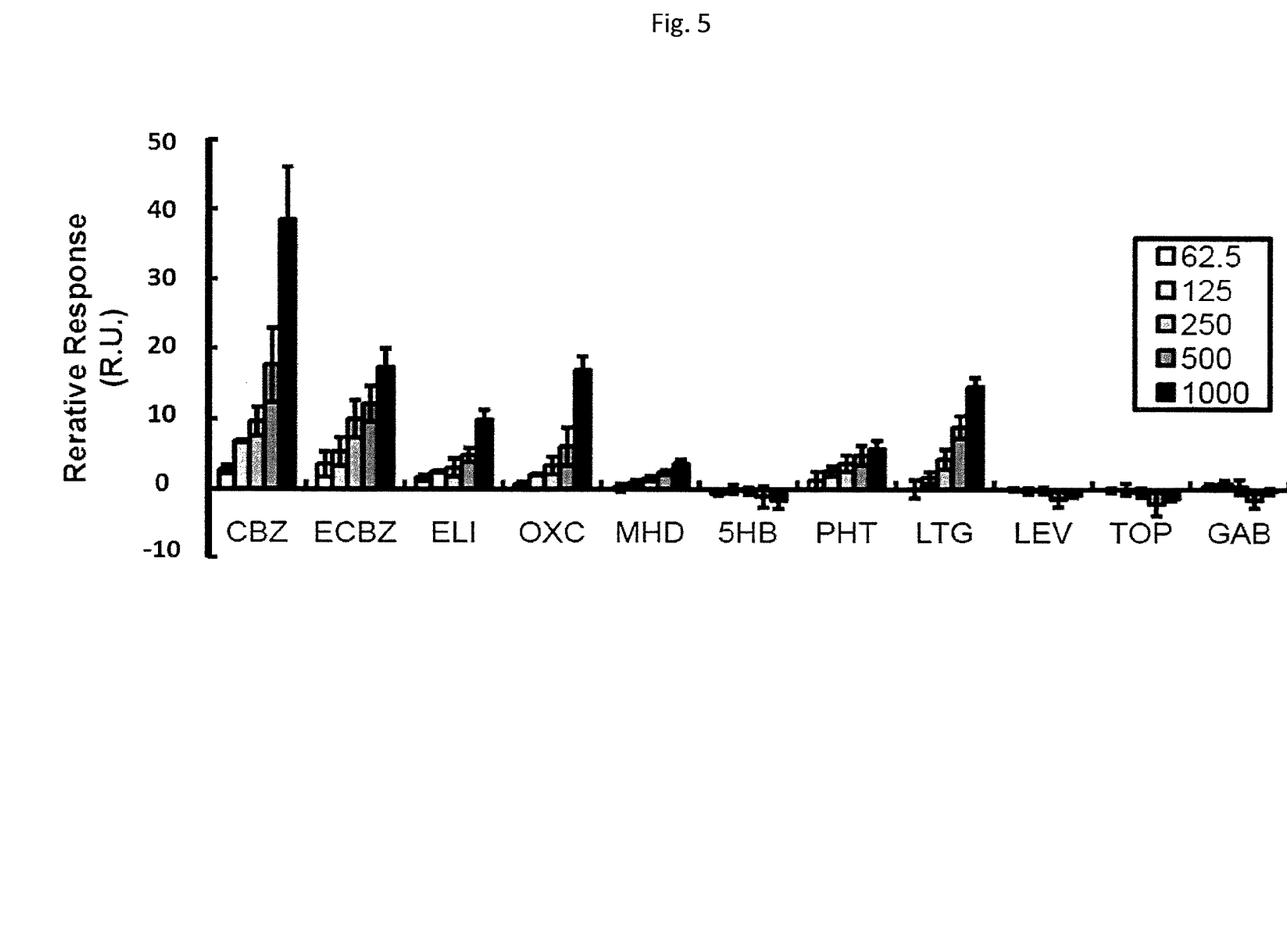
FIG. 5 is a chart showing binding of CBZ and its analogs at various concentrations (62.5 to 1000 μM) to soluble HLA-B*1502 coated on a CM5 chip. Relative responses (R.U.) were calculated by the standard DMSO solvent correction curve using a T100 evaluation software from four to seven independent experiments.

In order to further understand how HLA-B*1502 recognize and present CBZ analogs in the absence of antigen-processing mechanism, the direct interaction between HLA-B*1502 proteins and drugs was examined via surface plasmon resonance (SPR) analysis. 5 soluble forms of HLA-B molecules (sHLA-B*1501, 1502, 1503, 4001, and 5101) and 11 different chemicals (CBZ, ECBZ, OXC, ELI, MHD, 5HB, PHT, LTG, LEV, TOP, and GAB) were used for this biomolecular interaction analysis. The SPR screening data demonstrated that HLA-B*1502 was able to interact with all CBZ analogs directly except 5HB. See FIG. 5. Comparing with its analogs, CBZ has stronger binding ability toward HLA-B*1502; OXC, ECBZ and ELI had moderate binding ability, and MHD exhibited the weakest interaction. Similar to the functional and genetic studies, both PHT and LTG showed moderate HLA-B*1502 binding ability. LEV, TOP and GAB, the three drugs rarely known to cause SJS/TEN did not bind to the HLA-B*1502 or other HLA-B molecules at therapeutic concentrations.

(v) Direct CBZ Interaction is HLA-B*1502-Specific

Figure 6:
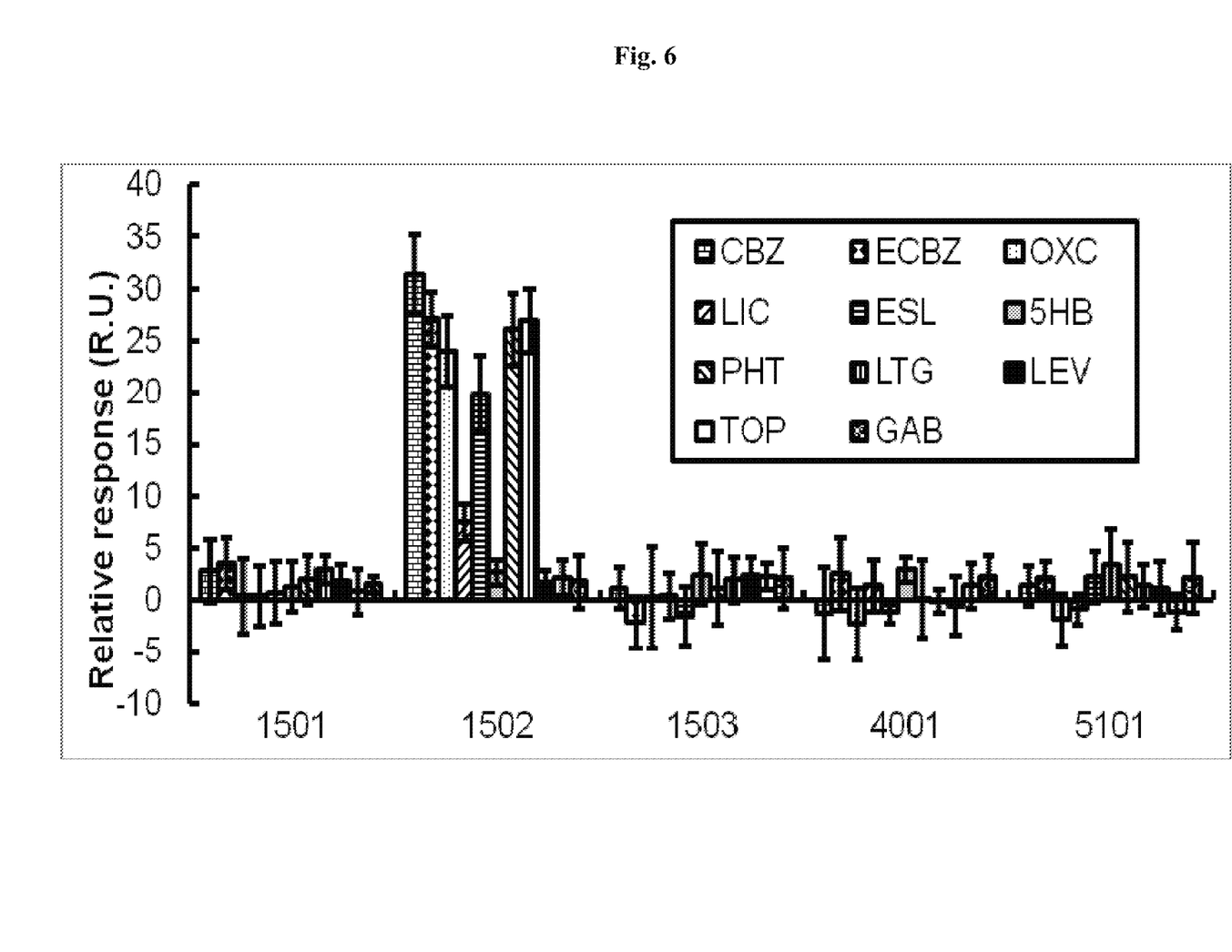
FIG. 6 is a chart showing binding of CBZ and its analogs to various HLA-B molecules. Data shown in the chart represents the mean±standard error of the mean (SEM) of four to eleven independent experiments.

Binding between CBZ or its analogs and HLA-B*1502 or HLA molecules related to it was examined following the method described above. The result shows that neither CBZ nor its seven analogs (see the Compounds section above) binds to HLA-B*1501 and HLA-B*1503, two HLA molecules closely related to HLA-B*1502. Two other common HLA-B molecules in Han Chinese population, i.e., HLA-B*4001 and HLA-B*5101, also did not bind to CBZ and its analogs. See FIG. 6. These results indicate the CBZ and its analogs specifically bind to HLA-B*1502. This is consistence with the genetic data showing that individuals carrying the HLA-*1502 allele are at risk for developing SJS/TEN when received these AEDs. See, Chung et al., Nature 428:486 (2004); and U.S. Pat. No. 7,470,513.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for identifying an HLA complex that binds to a small molecule compound, comprising:
   providing an HLA library including a plurality of HLA complexes located at a plurality of addresses on a support member, each of the HLA complexes being assigned to a distinct address;
   contacting a small molecule compound with the HLA complexes;
   determining whether the compound binds to one of the HLA complexes; and
   identifying the one HLA complex that binds to the compound based on its address, providing that the compound binds to one of the HLA complexes.

2. The method of claim 1, wherein the HLA complexes are class I HLA complexes.

3. The method of claim 2, wherein the class I HLA complexes are HLA-B complexes.

4. The method of claim 1, wherein the HLA complexes are class II HLA complexes.

5. The method of claim 4, wherein the class II HLA complexes are HLA-DR complexes.

6. The method of claim 3, wherein the HLA-B complexes are attached to the support member.

7. The method of claim 6, wherein the HLA-B complexes each include only extracellular components.

8. The method of claim 7, wherein the determining step is performed by Surface Plasmon Resonance.

9. A method for assessing a risk of a small molecule compound for inducing an adverse drug reaction in a subject administered with the compound, comprising
   providing an HLA library including a plurality of HLA complexes located at a plurality of addresses on a support member, each of the HLA complexes being assigned to a distinct address;
   contacting the compound with the HLA complexes; and
   determining whether the compound binds to one of the HLA complexes; wherein binding of the compound to one of the HLA complexes indicates that the compound is at risk of inducing an adverse drug reaction in a subject administered with the compound.

10. The method of claim 9, further comprising identifying the one HLA complex that bind to the compound based on its address, providing that the compound binds to one of the HLA complexes.

11. The method of claim 9, wherein the HLA complexes are class I HLA complexes.

12. The method of claim 11, wherein the class I HLA complexes are HLA-B complexes.

13. The method of claim 9, wherein the HLA complexes are class II HLA complexes.

14. The method of claim 13, wherein the class II HLA complexes are HLA-DR complexes.

15. The method of claim 12, wherein the HLA-B complexes are attached to the support member.

16. The method of claim 15, wherein the HLA-B complexes each include only extracellular components.

17. The method of claim 15, wherein the determining step is performed by Surface Plasmon Resonance.

18. The method of claim 6, wherein the support member is a microchip.

19. The method of claim 15, wherein the support member is a microchip.

* * * * *